(12) United States Patent
Lama et al.

(10) Patent No.: US 9,115,179 B2
(45) Date of Patent: Aug. 25, 2015

(54) SYNTHESIS OF BETA-TURN PEPTIDOMIMETIC CYCLIC COMPOUNDS

(71) Applicant: Mimetogen Pharmaceuticals Inc., Montréal (CA)

(72) Inventors: Teresa Lama, Montreal (CA); Jeanick Pascal, San Diego, CA (US)

(73) Assignee: Mimetogen Pharmaceuticals Inc., Montreal, Quebec (CA)

( * ) Notice: Subject to any disclaimer, the term of this patent is extended or adjusted under 35 U.S.C. 154(b) by 18 days.

(21) Appl. No.: 13/913,084

(22) Filed: Jun. 7, 2013

(65) Prior Publication Data
US 2013/0345395 A1    Dec. 26, 2013

Related U.S. Application Data

(60) Provisional application No. 61/663,387, filed on Jun. 22, 2012.

(51) Int. Cl.
| | |
|---|---|
| A61K 38/04 | (2006.01) |
| C07K 5/00 | (2006.01) |
| C07K 7/00 | (2006.01) |
| C07K 16/00 | (2006.01) |
| C07K 17/00 | (2006.01) |
| A61K 38/00 | (2006.01) |
| C07K 7/54 | (2006.01) |
| C07K 7/56 | (2006.01) |

(52) U.S. Cl.
CPC .... C07K 7/54 (2013.01); C07K 7/56 (2013.01)

(58) Field of Classification Search
None
See application file for complete search history.

(56) References Cited

U.S. PATENT DOCUMENTS

| 5,990,278 | A  * | 11/1999 | Hoffmann et al. ............. 530/333 |
| 6,881,719 | B2 | 4/2005 | Saragovi et al. |
| 2003/0211982 | A1 * | 11/2003 | Saragovi et al. .................. 514/9 |

OTHER PUBLICATIONS

Maliartchouk et al. A Designed Peptidomimetic Agonistic Ligand of TrkA Nerve Growth Factor Receptors. Molecular Pharmacology, 2007, vol. 57, pp. 385-391.*
Albericio et al. Fmoc Methodology: Cleavage from the Resin and Final Deprotection in Amino Acids, Peptides and Proteins in Organic Chemistry, vol. 3. 2011. pp. 349-369.*
Albericio et al. Solid supports for the synthesis of peptides. Supplement to Chimica Oggi/Chemistry Today, vol. 26, No. 4, 2008, pp. 29-34.*
Feng et al. SnAr Cyclizations to Form Cyclic Peptidomimetics of beta-turns. JACS, 1998, vol. 120, pp. 10768-10769.*
Colangelo, Anna Maria, et al., A New Nerve Growth Factor-Mimetic Peptide Active on Neuropathic Pain in Rats, The Journal of Neuroscience, 2008, 28(11):2698-2709.
Feng, Yangbo, et al., Solid-Phae S(subscript)NAr Macrocyclizations to Give Turn—Extended-Turn Peptidomimetics, Chem. Eur. J., 1999, 5(11):3261-3272.

* cited by examiner

*Primary Examiner* — Marcela M Cordero Garcia
(74) *Attorney, Agent, or Firm* — Pillsbury Winthrop Shaw Pittman LLP

(57) ABSTRACT

The present invention relates to methods of preparing β-turn cyclic peptidomimetic compounds and intermediates thereof. Particularly, the present invention relates to a process for the synthesis of β-turn cyclic peptidomimetic compounds of formula I:

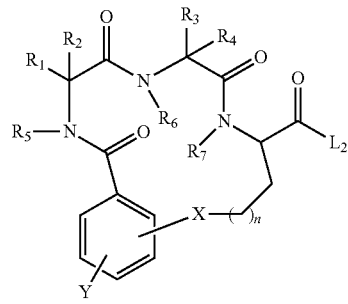

where $R_1, R_2, R_3, R_4, R_5, R_6, R_7, L_2, X, Y$ and n are as defined in the specification.
The present invention provides a more efficient route for preparing β-turn cyclic peptidomimetic compounds and intermediates thereof.

54 Claims, 2 Drawing Sheets

Scheme 1:

SYNTHESIS OF BETA-TURN PEPTIDOMIMETIC CYCLIC COMPOUNDS

RELATED APPLICATIONS

This application claims priority to application Ser. No. 61/663,387, filed Jun. 22, 2012, which is expressly incorporated by reference herein in its entirety

FIELD OF THE INVENTION

The present invention relates to methods of preparing β-turn cyclic peptidomimetic compounds and intermediates thereof.

INTRODUCTION

Although the synthesis of certain β-turn cyclic peptidomimetic compounds are known, when these methodologies are applied to the large scale production of compounds in grams and kilograms quantities, which is required for in vivo and clinical studies, difficulties arise, especially with respect to the formation of dimeric side product.

Considering the promising pharmacological activity of several compounds in the class of β-turn cyclic peptidomimetic compounds, there exits a need for the development of a new synthetic methodology that allows for more cost effective production.

It is therefore an aspect of this invention to provide new synthetic methods for the preparation of β-turn cyclic peptidomimetic compounds, which overcomes the disclosed limitations. It is a further aspect of this invention to provide commercially viable methods to produce these compounds.

SUMMARY OF THE INVENTION

Figure 1:
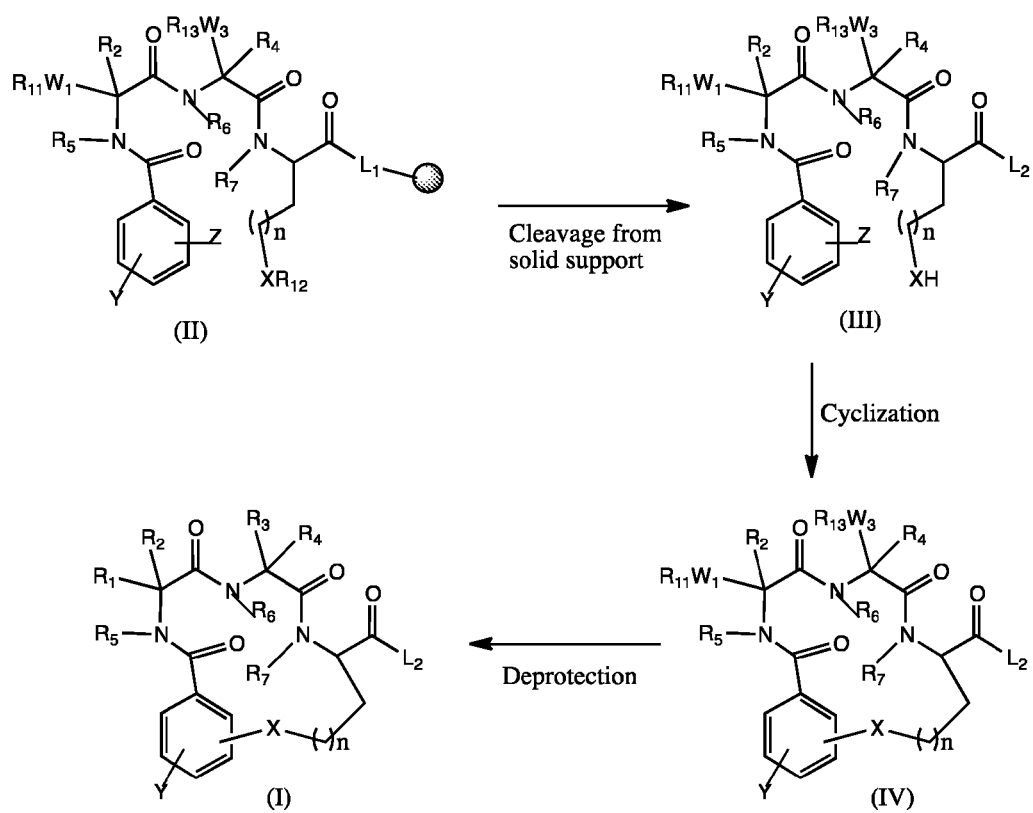
FIG. 1 shows a general reaction Scheme 1, depicts a reaction leading to β-turn cyclic peptidomimetic compounds of formula (I), according to embodiments of the present invention.

In various embodiments, the invention provides synthetic methods for β-turn cyclic peptidomimetic compounds. In other embodiments, the invention provides intermediate compounds useful in the method. Synthetic methods and novel intermediates are illustrated in the embodiments denoted in FIG. 1 (Scheme 1).

Certain embodiments of the present invention provide a method of preparing a β-turn peptidomimetic cyclic compound of formula (I)

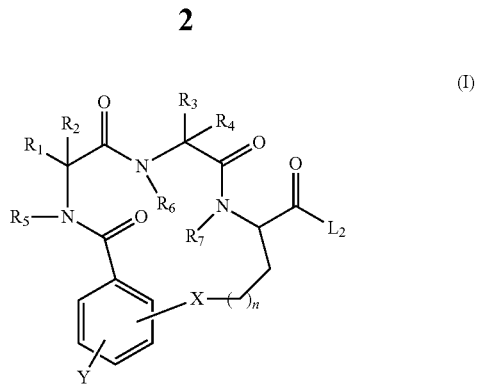

(I)

the method comprising steps of:
(a) providing a protected linear peptidomimetic compound of formula (III)

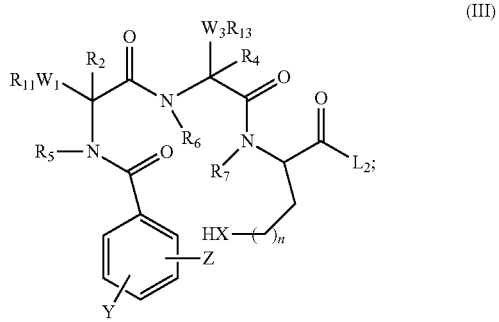

(III)

(b) cyclizing the protected linear peptidomimetic compound of formula (III) to form a protected β-turn peptidomimetic cyclic compound of formula (IV) by an intramolecular aromatic nucleophilic substitution

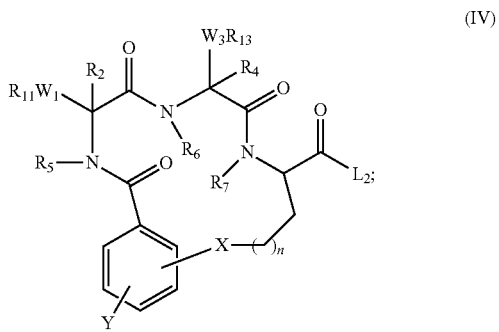

(IV)

and
(c) deprotecting an amino acid side chain protecting group in the protected β-turn peptidomimetic cyclic compound of formula (IV);
wherein:
$R_1$ and $R_3$ can independently be hydrogen, $C_1$ to $C_6$ alkyl, aryl, or an amino acid side chain substituent of a natural or unnatural amino acid;
$R_2$ and $R_4$ can independently be hydrogen or $C_1$ to $C_6$ alkyl, or $R_1$ and $R_2$ together with the carbon atom to which they are attached form a cyclopropyl, cyclobutyl, cyclopentyl or cyclohexyl group, or $R_3$ and $R_4$ together with the carbon atom to which they are attached form a cyclopropyl, cyclobutyl, cyclopentyl or cyclohexyl group;

$R_5$, $R_6$ and $R_7$ can independently be hydrogen or $C_1$ to $C_6$ alkyl;

Y can be hydrogen, —$NO_2$, —$COOR_8$, —$OC(R_8)_3$, —$SO_3R_8$, or —$SO_2R_8$;

each $R_8$ can be alkyl or aryl;

X can be O, N, S, P, Se, C, $C_1$ to $C_6$ alkylene, SO, $SO_2$ or NH;

Z can be F, Cl, Br or I;

$R_{11}$ and $R_{13}$ can independently be hydrogen or a protecting group;

$W_1$ and $W_3$ can independently be an amino acid side chain substituent of a natural or unnatural amino acid, less a hydrogen atom at the point of attachment to $R_{11}$ and $R_{13}$ respectively;

n can be 0, 1, 2, 3, 4 or 5; and $L_2$ can be H, $NH_2$, OH, SH, COOH, NH—$CH_2$—COOH, $C_1$ to $C_6$ alkyl, or $C_1$ to $C_6$ aryl.

In certain embodiments, a protected linear peptidomimetic compound attached to a solid support of formula (II) is provided:

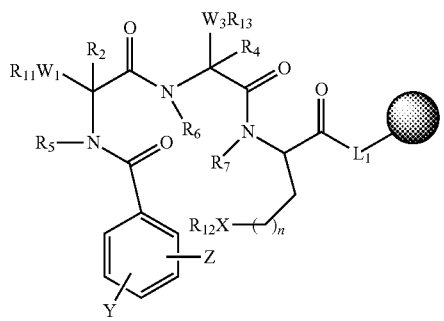

(II)

wherein:

$R_2$ and $R_4$ can independently be hydrogen or $C_1$ to $C_6$ alkyl, or $W_1$ and $R_2$ together with the carbon atom to which they are attached form a cyclopropyl, cyclobutyl, cyclopentyl or cyclohexyl group, or $W_3$ and $R_4$ together with the carbon atom to which they are attached form a cyclopropyl, cyclobutyl, cyclopentyl or cyclohexyl group;

$R_5$, $R_6$ and $R_7$ can independently be hydrogen or $C_1$ to $C_6$ alkyl;

Y can be hydrogen, —$NO_2$, —$COOR_8$, —$OC(R_8)_3$, —$SO_3R_8$, or —$SO_2NR_8$;

wherein each $R_8$ can independently be alkyl or aryl;

X can be O, N, S, P, Se, C, $C_1$-$C_6$ alkylene, SO, $SO_2$ or NH;

Z can be F, Cl, Br or I;

$R_{11}$, $R_{12}$ and $R_{13}$ can independently be hydrogen or a protecting group;

$W_1$ and $W_3$ can independently be an amino acid side chain substituent of a natural or unnatural amino acid, less a hydrogen atom;

n can be 0, 1, 2, 3, 4 or 5; and $L_1$ can be null, NH, O, S, COO—, NH—$CH_2$—COO—, $C_1$ to $C_6$ alkylene, or $C_1$ to $C_6$ arylene;

wherein the solid support is a resin comprising a functional group selected from a group consisting of 2-chlorotrityl chloride (2-CTC), 4-hydroxymethyl-3-methoxyphenoxybutirric acid MBHA (HMPB-MBHA), 9-Fmoc-amino-xanthen-3-yloxy-Merrifield resin (Sieber Amide), trityl alcohol, 4-methyltrityl chloride, 4-methoxytrityl chloride, 4-(2',4'-Dimethoxyphenyl-hydroxymethyl)-phenoxy resin (Rink acid resin), 2-methoxy-4-alkoxybenzyl alcohol resin (Sasrin® resin), 3-(N-Fmoc-N-methoxy)propyl-amidomethyl resin (Weinreb amide resin).

In certain embodiments, a protected linear peptidomimetic compound of formula (III) is provided:

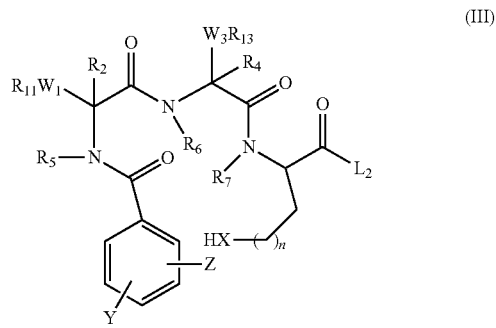

(III)

wherein:

$R_2$ and $R_4$ can independently be hydrogen or $C_1$ to $C_6$ alkyl, or $W_1$ and $R_2$ together with the carbon atom to which they are attached form a cyclopropyl, cyclobutyl, cyclopentyl or cyclohexyl group, or $W_3$ and $R_4$ together with the carbon atom to which they are attached form a cyclopropyl, cyclobutyl, cyclopentyl or cyclohexyl group;

$R_5$, $R_6$ and $R_7$ can independently be hydrogen or $C_1$ to $C_6$ alkyl;

Y can be hydrogen, —$NO_2$, —$COOR_8$, —$OC(R_8)_3$, —$SO_3R_8$, or —$SO_2NR_8$;

each $R_8$ can independently be alkyl or aryl;

X can be O, N, S, P, Se, C, $C_1$ to $C_6$ alkylene, SO, $SO_2$ or NH;

Z can be F, Cl, Br or I;

$R_{11}$ and $R_{13}$ can independently be hydrogen or a protecting group;

$W_1$ and $W_3$ can independently be an amino acid side chain substituent of a natural or unnatural amino acid, less a hydrogen atom at the point of attachment to $R_{11}$ and $R_{13}$ respectively;

n can be 0, 1, 2, 3, 4 or 5; and $L_2$ can be H, $NH_2$, OH, SH, COOH, NH—$CH_2$—COOH, $C_1$ to $C_6$ alkyl, or $C_1$ to $C_6$ aryl.

In certain embodiments, a protected β-turn peptidomimetic cyclic compound of formula (IV) is provided:

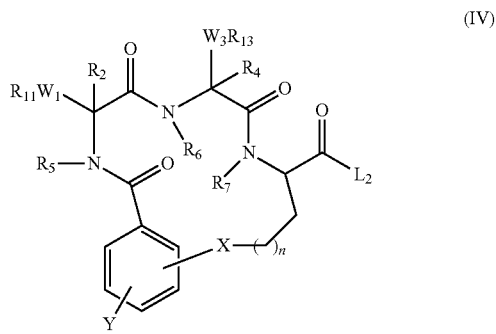

(IV)

wherein:

$R_2$ and $R_4$ can independently be hydrogen or $C_1$ to $C_6$ alkyl, or $W_1$ and $R_2$ together with the carbon atom to which they are attached form a cyclopropyl, cyclobutyl, cyclopentyl or cyclohexyl group, or $W_3$ and $R_4$ together with the carbon atom to which they are attached form a cyclopropyl, cyclobutyl, cyclopentyl or cyclohexyl group;

$R_5$, $R_6$ and $R_7$ can independently be hydrogen or $C_1$ to $C_6$ alkyl;

Y can be hydrogen, —$NO_2$, —$COOR_8$, —$OC(R_8)_3$, —$SO_3R_8$, or —$SO_2NR_8$;

each $R_8$ can independently be alkyl or aryl;

X can be O, N, S, P, Se, $C_1$ to $C_6$ alkylene, SO, $SO_2$ or NH;

Z can be F, Cl, Br or I;

$R_{11}$ and $R_{13}$ can independently be hydrogen or a protecting group;

$W_1$ and $W_3$ can independently be an amino acid side chain substituent of a natural or unnatural amino acid, less a hydrogen atom;

n can be 0, 1, 2, 3, 4 or 5; and $L_2$ can be H, $NH_2$, OH, SH, COOH, NH—$CH_2$—COOH, $C_1$ to $C_6$ alkyl, or $C_1$ to $C_6$ aryl.

DESCRIPTION OF THE DRAWINGS

The drawings illustrate generally, by way of example, but not by way of limitation, various embodiments discussed in the present document.

FIG. 1 is a general schematic illustration of the synthetic methods for preparing β-turn peptidomimetic cyclic compound of formula (I) according to embodiments of the present invention.

Figure 2:
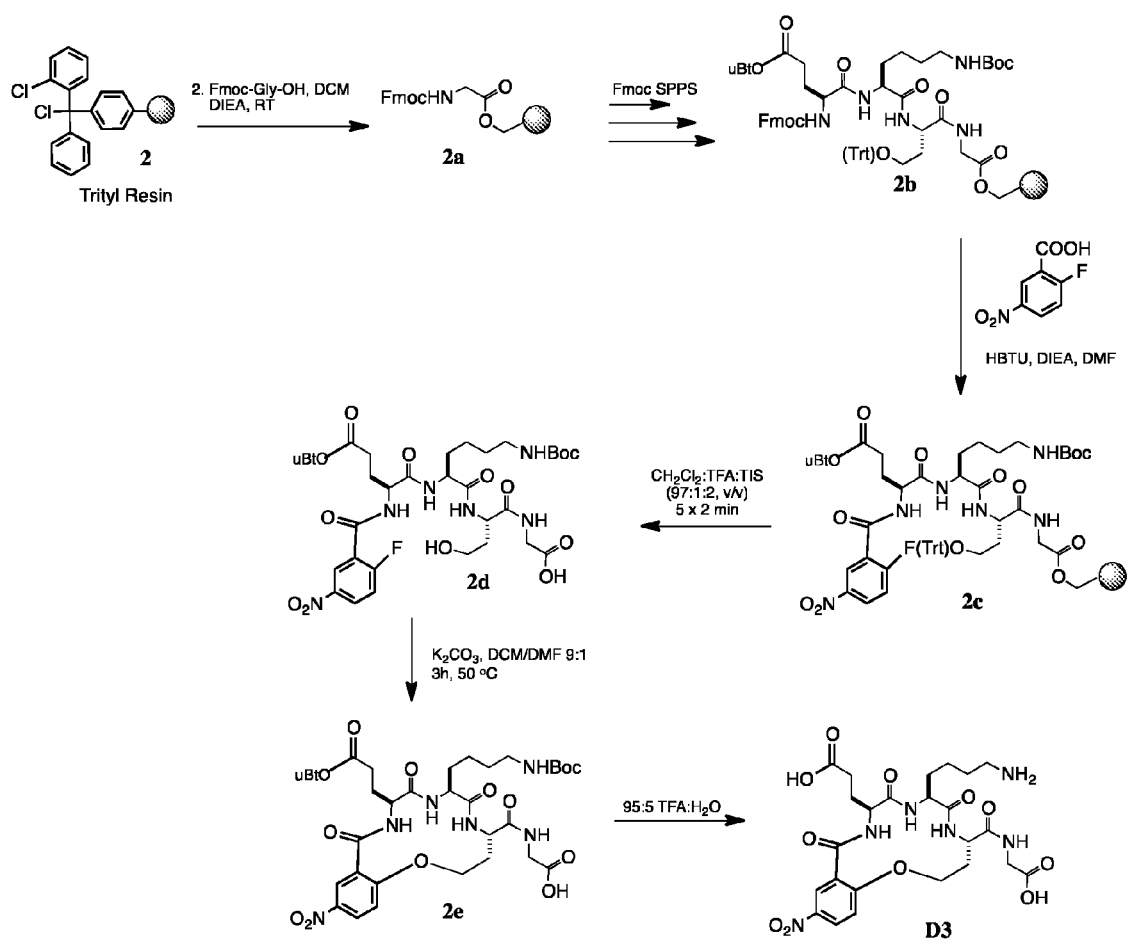
FIG. 2 shows an exemplary reaction Scheme 2, depicts a route to prepare β-turn peptidomimetic cyclic compound of structure D3 using 2-chlorotrityl chloride (2-CTC) resin, according to an embodiment of the present invention.

FIG. 2 is an exemplary reaction scheme for preparing β-turn peptidomimetic cyclic compound of structure D3 using 2-chlorotrityl chloride (2-CTC) resin according to an embodiment of the present invention.

DETAILED DESCRIPTION OF THE INVENTION

Definitions

As used herein, the terms "a" or "an" are used, as is common in patent documents, to include one or more than one, independent of any other instances or usages of "at least one" or "one or more."

As used herein, the term "about" refers to an amount that is approximately, nearly, almost, or in the vicinity of being equal to or is equal to a stated amount.

As used herein, the term "unnatural amino acid" refers to all amino acids which are not natural amino acids as described above. Such amino acids include the D-isomers of any of the 19 optically active and glycine naturally occurring amino acids described above. Unnatural amino acids also include homoserine, homocysteine, citrulline, 2,3-diaminopropionic acid, hydroxyproline, ornithine, norleucine, and thyroxine. Additional unnatural amino acids are well known to one of ordinary skill in the art. An unnatural amino acid may be a D- or L-isomer. An unnatural amino acid may also be an alpha amino acid, a beta amino acid or a gamma amino acid. An unnatural amino acid may also be a post-translationally modified amino acid, such as a phosphorylated serine, threonine or tyrosine, an acylated lysine, or an alkylated lysine or arginine. Many forms of post-translationally modified amino acids are known.

As used herein, the term "protecting group" means that a particular functional moiety, e.g., O, S, or N, is temporarily blocked so that a reaction can be carried out selectively at another reactive site in a multifunctional compound.

As used herein, the term "protic solvent" refers to a solvent that carries hydrogen attached to oxygen as in a hydroxyl group or attached to nitrogen as in an amine group. Such solvents can donate an H+ (proton). Examples of protic solvents include water, ethanol, tert-butanol, and diethylamine.

As used herein, the term "aprotic solvent" refers to a solvent that carries few or no hydrogen attached to oxygen as in a hydroxyl group or attached to nitrogen as in an amine group.

As used herein, the term "ring" means a compound whose atoms are arranged in formulas in a cyclic form.

As used herein, the term "alkyl" means a hydrocarbon group that may be linear, cyclic, branched, or a combination thereof having the number of carbon atoms designated (i.e., $C_1$-$C_6$ means one to six carbon atoms). Examples of alkyl groups include methyl, ethyl, n-propyl, isopropyl, n-butyl, t-butyl, isobutyl, sec-butyl, pentyl, iso-amyl, hexyl, octyl, noyl and the like. Alkyl groups may be optionally substituted as defined herein. The term "alkylene," as used herein, refers to a saturated aliphatic group derived from a straight or branched chain saturated hydrocarbon attached at two or more positions, such as methylene (—$CH_2$—).

As used herein, the term "allyl" refers to compound containing the allyl group (i.e., $CH_2$=CH—$CH_2$—).

As used herein, the term "aryl" means a carbocyclic aromatic system containing one, two or three rings wherein such rings may be attached together in a pendent manner or may be fused. The term "aryl" embraces aromatic radicals such as benzyl, phenyl, naphthyl, anthracenyl, phenanthryl, indanyl, indenyl, annulenyl, azulenyl, tetrahydronaphthyl, and biphenyl. Aryl groups may be optionally substituted as defined herein. The term "arylene" designates any divalent group derived from aryl (such as above defined) by abstracting a hydrogen atom.

When a group is defined to be "null," this means that the group is absent.

When a group is substituted, the substituents may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, cyano, hydrogen, halogen, hydroxy, amino, lower alkylamino, arylamino, amido, nitro, thiol, lower alkylthio, arylthio, lower alkylsulfinyl, lower alkylsulfonyl, arylsulfinyl, arylsulfonyl, arylthio, sulfonate, sulfonic acid, trisubstituted silyl, $N_3$, SH, $SCH_3$, $C(O)CH_3$, pyridinyl, thiophene, furanyl, lower carbamate, and lower urea.

For purposes of clarity and as an aid in understanding the invention, as disclosed and claimed herein, the following terms and abbreviations are defined below:

Boc—t-butyloxycarbonyl
Cbz—benzyloxycarbonyl
CTC—chlorotrityl chloride
DBU—1,8-Diazobicyclo[5.4.0]undec-7-ene
DCM—dichloromethane
DIC—1,3-Diisopropylcarbodiimide
DIEA—N,N-diisopropylethylamine
DIPEA—N,N-diisopropylethylamine
DMF—dimethylformamide
Fmoc—9-fluorenylmethoxycarbonyl
HBTU—O-Benzotriazole-N,N,N',N'-tetramethyl-uronium-hexafluoro-phosphate
HMPB-MBHA—4-Hydroxymethyl-3-methoxyphenoxybutirric acid MBHA, or 4-(4-hydroxymethyl-3-methoxyphenoxy)-butyryl-p-methyl-benzhydrylamine
HOBt—N-hydroxybenzotriazole
Mtt—methyltrityl
Pbf—pentamethyldihydrobenzofuransulfonyl
SPPS—solid phase peptide synthesis TBAF—tetrabutylammonium fluoride
TBDMS—tert-butyldimethylsilane
tBu—tert-Butyl ester
TFA—trifluoroacetic acid
THF—tetrahydrofuran
TIS—triisopropylsilane
TMG—tetramethylguanidine
Trt—trityl FIG. 1 shows Scheme 1, depicting general routes that were explored to prepare β-turn peptidomimetic cyclic compound of formula (I), including the steps of: (a) providing a protected linear peptidomimetic compound of formula (III); (b) cyclizing the protected linear peptidomimetic compound of formula (III) to form a protected β-turn peptidomimetic cyclic compound of formula (IV) by an intramolecular aromatic nucleophilic substitution; and (c) deprotecting an amino acid side chain protecting group in the protected β-turn peptidomimetic cyclic compound of formula (IV).

In certain embodiments, the invention provides a method of preparing a β-turn peptidomimetic cyclic compound of formula (I) having a macrocyclic ring of from 14 to 16 ring atoms.

In certain embodiments, the method provides compounds where $R_1$ and $R_3$ are amino acid side-chain substituents. Typically, $R_1$ and $R_3$ are independently derived from natural or unnatural amino acids. For example, $R_1$ and $R_3$ can independently be derived from the twenty naturally occurring protein amino acids (natural), or modified amino acids (unnatural), in either enantiomeric configuration. The twenty natural amino acids are alpha-amino acids which include glycine (Gly), alanine (Ala), valine (Val), leucine (Leu), isoleucine (Ile), lysine (Lys), arginine (Arg), histidine (His), proline (Pro), serine (Ser), threonine (Thr), phenylalanine (Phe), tyrosine (Tyr), tryptophan (Trp), aspartic acid (Asp), glutamic acid (Glu), asparagine (Asn), glutamine (Gln), cysteine (Cys) and methionine (Met). The generic structure of an alpha-amino acid is illustrated by Formula A: $H_2NCH(R^*)COOH$. $R^*$ represents the side chain substituent of the amino acid, which refers to as either $R_1$ or $R_3$ in the present disclosure.

An unnatural amino acid typically is any structure having Formula A wherein the $R^*$ group is any substituent other than one used in the twenty natural amino acids. See for instance, Biochemistry by L. Stryer, 31(1 ed. 1988), Freeman and Company, New York, for structures of the twenty natural amino acids. Unnatural amino acids also can be naturally occurring compounds other than the twenty alpha-amino acids above.

Such unnatural amino acids include the D-isomers of any of the 19 optically active and glycine naturally occurring amino acids described above. Unnatural amino acids also include homoserine, homocysteine, 2,3-diaminopropionic acid, citrulline, hydroxyproline, ornithine, norleucine, and thyroxine. Additional unnatural amino acids are well known to one of ordinary skill in the art. An unnatural amino acid may be a D- or L-isomer. An unnatural amino acid may also be a beta amino acid or a gamma amino acid having Formula B: $H_2N(CH)_n(R^*)COOH$ wherein n is equal to 2 or 3 and $R^*$ represents the side chain substituent of any of the twenty proteinogenic amino acids or any substituent other than one used in the twenty natural amino acids. An unnatural amino acid may also be a post-translationally modified amino acid, such as a phosphorylated serine, threonine or tyrosine, an acylated lysine, or an alkylated lysine or arginine. Many forms of post-translationally modified amino acids are known.

In certain embodiments, the method provides compounds where $R_1$ and $R_3$ are independently a side chain substituent of two different amino acids. In certain of such embodiments, $R_1$ and $R_3$ are independently a side chain substituent of lysine, glutamic acid, tyrosine, isoleucine, asparagine, arginine or threonine. In certain embodiments, $R_1$ and $R_3$ are independently a side chain substitutent of glutamic acid, lysine, isoleucine or arginine. In one embodiment, $R_1$ and $R_3$ are independently a side chain substitutent of glutamic acid or lysine. In another embodiment, $R_1$ and $R_3$ are independently a side chain substitutent of isoleucine or arginine.

In general, the amino acid side-chain substituents ($R_1$ and $R_3$) are protected by suitable protecting groups ($R_{11}$ and $R_{13}$, respectively) prior to the cyclization step in the method of preparing β-turn cyclic peptidomimetic compounds of the present invention. When the amino acid side-chain substituents, $R_1$ and $R_3$, are protected, they are represented as $W_1R_{11}$ and $W_3R_{33}$ respectively, where $W_1$ and $W_3$ are independently an amino acid side chain substituent of a natural or unnatural amino acid, less one hydrogen atom at the point of attachment to $R_{11}$ and $R_{13}$, respectively. The one hydrogen atom is usually found in a functional group such as carboxylic acid, amine, thiol, amide, hydroxyl and guanidine of the amino acid side-chain substituents.

Amino acid side-chain protection of any other sensitive reactive groups of any molecule involved in the synthesis at any step of the method described in the present invention can be achieved by means of conventional protecting groups known in the art such as those described by T. W. Greene & P. G. M. Wuts (Protective Groups In Organic Synthesis 1991, John Wiley and Sons, New-York); and by Sewald and Jakubke (Peptides: chemistry and Biology, 2002, Wiley-VCH, Wheinheim p. 142). For example, alpha amino protecting groups include, but are not limited to, acyl type protecting groups (e.g., trifluoroacetyl, formyl, acetyl), aliphatic urethane protecting groups (e.g., t-butyloxycarbonyl (Boc), cyclohexyloxycarbonyl), aromatic urethane type protecting groups (e.g., fluorenyl-9-methoxy-carbonyl (Fmoc), benzyloxycarbonyl (Cbz), Cbz derivatives) and alkyl type protecting groups (e.g., triphenyl methyl, benzyl).

Amino acids side chain protecting groups may include tert-butyl ether for serine, threonine, and tyrosine; Boc for lysine, tryptophan, and histidine; trityl for serine, threonine asparagine, glutamine, cysteine and histidine; tert-butyl or allyl ester for aspartate and glutamate, Pbf for arginine; benzyl for threonine and serine; Cbz for tyrosine, threonine, serine, arginine, and lysine; alkyl silane for serine and threonine; and all other protecting groups well known in the art.

In certain embodiments, the method provides compounds where $R_{11}$ and $R_{13}$ are independently selected from the group consisting of trifluoroacetyl, formyl, acetyl, t-butyloxycarbonyl (BOC), cyclohexyloxycarbonyl, fluorenyl-9-methoxycarbonyl (Fmoc), benzyloxycarbonyl (Cbz), Cbz derivatives, triphenyl, methyl, benzyl, allyloxycarbonyl, tert-butyl, alkyl silane and allyl.

In certain embodiments, the method provides compounds where $R_1$ is a side chain substitutent of glutamic acid, and $R_{11}$ is allyl or tert-butyl. In certain of such embodiments, $R_1$ is a side chain substitutent of glutamic acid, and $R_{11}$ is tert-butyl.

In certain embodiments, the method provides compounds where $R_3$ is a side chain substitutent of lysine and $R_{13}$ is benzyloxycarbonyl, allyloxycarbonyl, or tert-butyloxycarbonyl (BOC). In certain of such embodiments, $R_3$ is a side chain substitutent of lysine and $R_{13}$ is tert-butyloxycarbonyl (BOC).

The protecting groups may be removed at a convenient subsequent stage using methods known in the art. In certain embodiments, the protecting groups of the amino acid side chains $R_1$ and $R_3$ are not removed under the same condition used to cleave the peptidomimetic compound from the solid support. In certain of such embodiments, the protecting groups of the amino acid side chains $R_1$ and $R_3$ are not removed under the same acidic condition used to cleave the peptidomimetic compound from the solid support.

In certain embodiments, the method provides compounds where $R_2$ and $R_4$ are independently hydrogen or $C_1$ to $C_6$ alkyl.

In certain embodiments, the method provides compounds where $R_5$, $R_6$ and $R_7$ are hydrogen.

In certain embodiments, the method provides compounds where X is O, S or NH.

In certain embodiments, the method provides compounds where $L_1/L_2$ is a linking group effective to form dimers of the β-turn peptidomimetic cyclic compound of formula (I) by reaction with a homo bi-functional compound. Suitable $L_1$ includes null, NH, O, S, COO, NH—$CH_2$—COO—, $C_1$ to $C_6$ alkylene, or $C_1$ to $C_6$ arylene. In certain embodiments, $L_1$ is NH—$CH_2$—COO—. Suitable $L_2$ includes H, $NH_2$, OH, SH, COOH, NH—$CH_2$—COOH, $C_1$ to $C_6$ alkyl, or $C_1$ to $C_6$ aryl. In certain embodiments, $L_2$ is NH—$CH_2$—COOH.

In certain embodiments, the method provides compounds where n is 1.

In certain embodiments, the method provides compounds where Y is attached to the benzene ring of the formulas at the meta position relative to the point of attachment of the amide group. In certain embodiments, Y is —$NO_2$.

In certain embodiments, the method provides compounds where Z is attached to the benzene ring of the formulas at the ortho position relative to the point of attachment of the amide group. In certain embodiments, Z is F.

Cleavage from Solid Support

Referring to FIG. 1 (Scheme 1), the protected linear peptidomimetic compound of formula (III) can be obtained from cleaving a protected linear peptidomimetic compound of formula (II), wherein the protected linear peptidomimetic compound of formula (II) has the following structure:

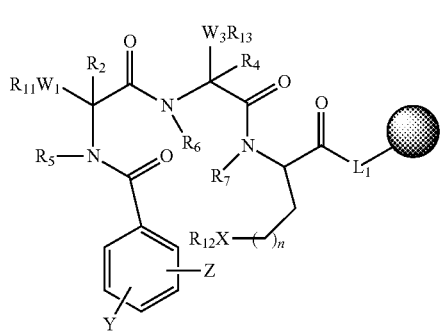

(II)

The cleaving from the solid support may be carried out in the presence of an acid, a base or a nucleophile.

Upon treatment with a cleaving solution, the protected linear peptidomimetic compound of formula (II) cleaves from the solid support to which it is attached via the linker group, $L_1$, to afford the linear peptidomimetic intermediate (III).

The solid support may be a resin which includes a functional group such as 2-chlorotrityl chloride (2-CTC), 4-hydroxymethyl-3-methoxyphenoxybutirric acid MBHA (HMPB-MBHA), 9-Fmoc-amino-xanthen-3-yloxy-Merrifield resin (Sieber Amide), trityl alcohol, 4-methyltrityl chloride, 4-methoxytrityl chloride, 4-(2',4'-Dimethoxyphenylhydroxymethyl)-phenoxy resin (Rink acid resin), 2-methoxy-4-alkoxybenzyl alcohol resin (Sasrin[200] resin), 3-(N-Fmoc-N-methoxy)propyl-amidomethyl resin (Weinreb amide resin). In certain embodiments, the resin comprising a functional group of 2-chlorotrityl chloride (2-CTC) or 2-methoxy-4-alkoxybenzyl alcohol resin (Sasrin®resin).

The resin used as solid support in the present invention may have a functional group loading of at least 0.75 mmol/g, for example, from 1.0 mmol/g to 2.0 mmol/g, or from 1.2 mmol/g to 1.6 mmol/g.

Typically, the resin is an insoluble polymer, such as, a crosslinked polystyrene/1% divinylbenzene co-polymer. However, polymers other than polystyrene based can also be used as solid support, such as pure or mixed PEG resins (e.g., Tentagel, NovaPEG and NovaSyn resins). These non-polystyrene based polymers can provide better swelling properties in a variety of different solvents.

The protected linear peptidomimetic compound of formula (II) is attached to the resin via a labile linkage, such as an acid labile ester linkage, while the functional amino acid side chains are protected using more stable protecting groups that are not cleaved or deprotected under the conditions required for the cleavage of the peptide from the resin. Such functional amino acid side chains can be protected with a strong acid labile protecting group on the functional groups. The protecting groups used on the functional amino acid side chains are described herein. Thus, the cleaving of the protected linear peptidomimetic compound of formula (II) does not cause significant deprotection of any protected functional group $R_{11}$ and $R_{13}$ present in formula (II).

In certain embodiments, the cleaving of the protected linear peptidomimetic compound of formula (II) is performed under mild acidic conditions. The cleaving solution may contain from about 0.01% to about 50% (v/v), from 0.1% to 10% (v/v), or from 0.5% to 5% (v/v) of an acid, such as, trifluoro acetic acid (TFA), or acetic acid.

The cleaving of the protected linear peptidomimetic compound of formula (II) may be carried out in different solvent systems. The solvent system is an organic solvent or a mixture of organic solvents. The solvent system may comprise a polar, aprotic solvent, such as, dichloromethane, acetonitrile or tetrahydrofurane and mixture thereof.

A scavenger can be added to the cleaving solution to prevent the alkylation of the X group by the alkyl-carbenium ion formed during the reaction. Suitable scavengers include, but are not limited to, triisopropylsilane (TIS), thioanisol, trialkylsilane (e.g., trimethylsilane, triethylsilane), or mixture thereof. In one embodiment, the scavenger is triisopropylsilane (TIS).

In certain embodiments, the mild acidic solution contains less than 10%, 5%, or 3% of a mixture of acid and scavenger. The relative ratio by volume of acidic material to scavenger in the mild acidic solution used in the cleaving of the protected linear peptidomimetic compound of formula (II) from the solid support can be from about 1:1 to about 1:5, from about 1:1 to about 1:3, or about 1:2. In one embodiment, the cleaving of the protected linear peptidomimetic compound of formula (II) is performed in a solution comprising less than 10% of a mixture of TFA and TIS in a ratio by volume of from about 1:1 to about 1:5.

In certain embodiments, the terminal functional group X may be protected (i.e., when $R_{12}$ is a protecting group). In certain embodiments, when X is O and $R_{12}$ is trityl (Trt), tert-butyldimethylsilane (TBDMS), or any protecting group that can be removed under conditions that do not cause deprotection of the other protecting groups present in the formula, such as mild acidic conditions. In certain of such embodiments, when X is O and $R_{12}$ is trityl (Trt), or tert-butyldimethylsilane (TBDMS). In certain embodiments, X is S and $R_{12}$ is trityl. In certain embodiments, X is NH and $R_{12}$ is 4-methyltrityl (Mtt).

In certain embodiments, the terminal functional group X may be deprotected upon treatment with the cleaving solution used to cleave the peptide from the solid support, thus affording the protected linear peptidomimetic compound of formula (III).

Cyclization

In one aspect of the invention, the cyclization reaction is performed in solution phase. Because the cyclization reaction is performed after the linear peptidomimetic intermediate (III) has been cleaved from the solid support, the loading of the resin is not critical in controlling the dimeric side product formation. For this reason, resins with a substitution grade having a functional group loading of as high as 2 mmol/g can be chosen as solid support. The use of higher loading resin improves the synthetic yield (i.e., increases the ratio of compound produced per gram of resin), thus reducing the production costs. The cyclization reaction may be carried out via an aromatic nucleophilic substitution reaction by the nucleophile X.

The cyclization reaction may be performed in polar protic solvents, such as, acetonitrile, tetrahydrofurane, DMF, mixtures of DCM/DMF, or mixtures thereof. The mixture of DCM/DMF may be used in the ratio of from about 5:95 to about 95:5, from about 70:30 to about 95:5, from about 80:20 to about 90:10. Significant amounts of solvents like water and methanol are to be avoided as they can act as nucleophiles and interfere with the cyclization. In one embodiment, the cyclization reaction is performed in the absence of water. In one embodiment, the cyclization reaction is performed in the absence of methanol. In one embodiment, the cyclization reaction is performed in the absence of water and methanol.

In certain embodiments, the cyclization reaction is a base-catalyzed cyclization reaction. The role of the base in the cyclization reaction is to increase the nucleophilic character of the functional group X. Examples of bases that can be used are $K_2CO_3$, $CsCO_3$, CsF, tetrabutylammonium fluoride (TBAF), tetramethylguanidine (TMG).

An important aspect of the cyclization step is to control the concentration of the linear peptidomimetic intermediate (III) during the reaction to avoid the formation of the dimeric side product. When the cyclization reaction is performed at higher concentrations of the linear peptidomimetic intermediate (III), e.g., greater than 0.05 M, the rate of intermolecular reaction increases, and thus accelerates the rate of dimeric side product formation. Consequently, to avoid the formation of dimers, the cyclization reaction may be performed at concentrations lower than 0.05 M, particularly, at concentrations lower than 0.03 M, or at concentrations lower than 0.02 M. Such low concentrations (i.e., high dilutions) may be achieved by using large volumes of solvents. Alternatively, the cyclization reaction may be performed by slow addition of the linear peptidomimetic intermediate (III) to the reaction media, which can avoid the usage of large volumes of solvent.

The cyclization reaction may be carried out at room temperature. Reaction time at room temperature can vary from 24 hours to 48 hours according to ring size, nucleophile involved in the reaction, base and solvent. Heating the reaction to higher temperatures, e.g., 40° C. to 60° C., may reduce the reaction time to 1-5 hours. Particularly, when the cyclization reaction is carried out at about from 45° C. to 55° C., the reaction time may be reduced to 2-4 hours. Typically, the cyclization reaction is carried out at a temperature from 20° C. to 65° C., from 25° C. to 60° C., or from 45° C. to 55° C.

The reaction can be monitored by analytical HPLC, LC-MS or UV as the linear peptidomimetic intermediate (III) and the β-turn peptidomimetic cyclic compound of formula (I) have different retention time, mass, and UV profile. Once the cyclization is completed, the solution may be filtered through, e.g., a Celite pad, to eliminate the base. The filter may be washed with a solvent, e.g., THF, and the organic layer may be then collected and evaporated under vacuum.

Deprotection

For the final deprotection of the amino acids side chain protecting groups, the protected β-turn peptidomimetic cyclic compound of formula (IV) is treated with appropriate reagents according to the type of protecting groups present in the formula. In one embodiment a strong acidic solution is used. Typically, the strong acidic solution includes greater than 50% TFA. TFA can be dissolved in water or in organic solvents, such as DCM, THF, etc. In certain embodiments, the strong acidic solution has a composition of TFA:$H_2O$ in a ratio by volume of from 90:10 to 99:1, from 90:10 to 95:5, or at about 95:5.

In certain embodiments, the strong acidic solution may further include a scavenger, such as triisopropylsilane (TIS), thioanisol, trialkylsilane (e.g., trimethylsilane, triethylsilane), or mixture thereof. In one embodiment, the scavenger is triisopropylsilane (TIS). After deprotection, the crude product can be precipitated using ether or methyltertbutylether at a temperature below 0° C., e.g., at about −20° C., and then filtered and purified by reverse-phase HPLC(RP-HPLC).

In one specific aspect, the present invention provides a method of preparing a β-turn peptidomimetic cyclic compound D3

D3

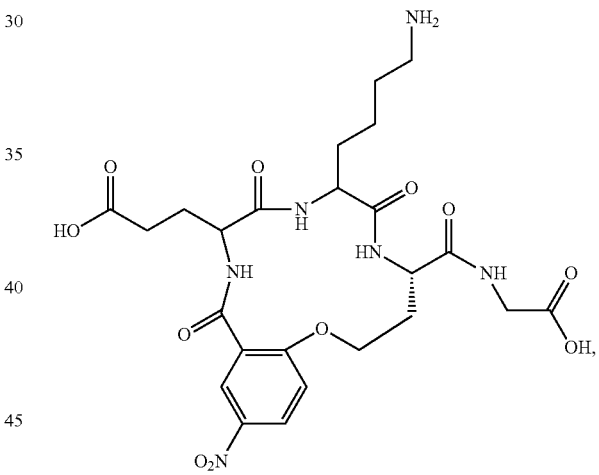

the method comprising steps of:

(a) providing a protected linear peptidomimetic compound of formula (IIIa)

(IIIa)

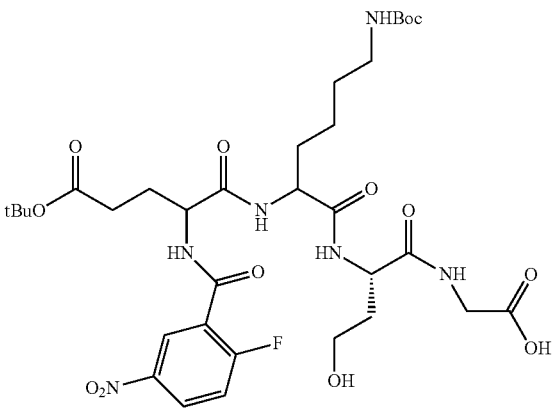

(b) cyclizing the protected linear peptidomimetic compound of formula (IIIa) to form a protected β-turn peptidomimetic cyclic compound of formula (IVa) by an intramolecular aromatic nucleophilic substitution

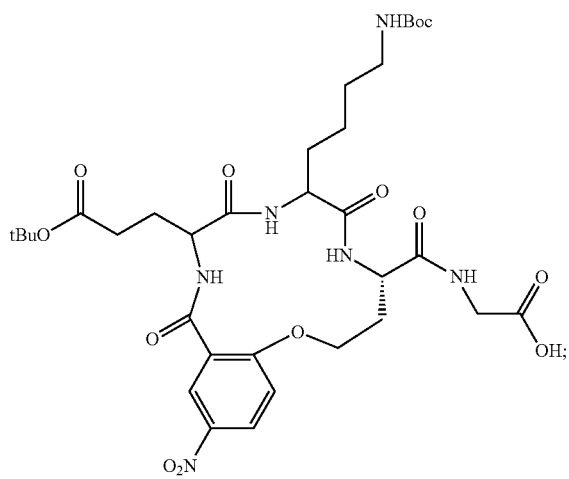

(IVa)

and (c) deprotecting an amino acid side chain protecting group in the protected β-turn peptidomimetic cyclic compound of formula (IVa).

In certain embodiments, a protected linear peptidomimetic compound attached to a solid support of formula (IIa) is provided:

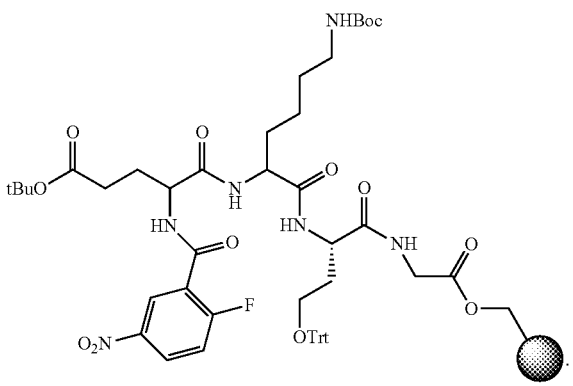

(IIa)

The invention also relates to intermediates which are used to prepare a β-turn peptidomimetic cyclic compound of formula (I). Disclosed herein are intermediates useful for preparing β-turn peptidomimetic cyclic compound of formula (I), and in specific embodiments, intermediates useful for preparing β-turn peptidomimetic cyclic compound D3.

Protected linear peptidomimetic compound of formula (II)

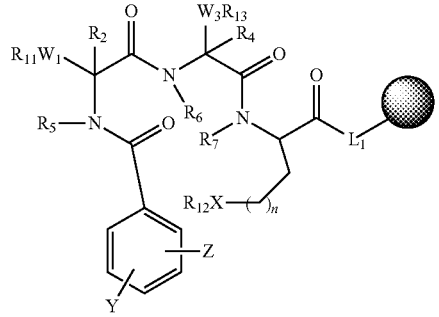

(II)

wherein $R_2$ and $R_4$ are independently hydrogen or $C_1$ to $C_6$ alkyl, or $W_1$ and $R_2$ together with the carbon atom to which they are attached form a cyclopropyl, cyclobutyl, cyclopentyl or cyclohexyl group, or $W_3$ and $R_4$ together with the carbon atom to which they are attached form a cyclopropyl, cyclobutyl, cyclopentyl or cyclohexyl group;

$R_5$, $R_6$ and $R_7$ are independently hydrogen or $C_1$ to $C_6$ alkyl;

Y is selected from the group consisting of hydrogen, $-NO_2$, $-COOR_S$, $-OC(R_8)_3$, $-SO_3R_8$, and $-SO_2NR_8$;

each $R_8$ is independently alkyl or aryl;

X is selected from the group consisting of O, N, S, P, Se, C, $C_1$ to $C_6$ alkylene, SO, $SO_2$ and NH;

Z is selected from the group consisting of F, Cl, Br and I;

$R_{11}$, $R_{12}$ and $R_{13}$ are independently hydrogen or a protecting group;

$W_1$ and $W_3$ are independently an amino acid side chain substituent of a natural or unnatural amino acid, less a hydrogen atom at the point of attachment to $R_{11}$ and $R_{13}$ respectively;

n is 0, 1, 2, 3, 4 or 5; and $L_1$ is selected from the group consisting of null, NH, O, S, COO, NH—$CH_2$—COO, $C_1$ to $C_6$ alkylene, and $C_1$ to $C_6$ arylene;

wherein the solid support is a resin comprising a functional group selected from a group consisting of 2-chlorotrityl chloride (2-CTC), 4-hydroxymethyl-3-methoxyphenoxybutirric acid MBHA (HMPB-MBHA), 9-Fmoc-amino-xanthen-3-yloxy-Merrifield resin (Sieber Amide), trityl alcohol, 4-methyltrityl chloride, 4-methoxytrityl chloride, 4-(2',4'-Dimethoxyphenyl-hydroxymethyl)-phenoxy resin (Rink acid resin), 2-methoxy-4-alkoxybenzyl alcohol resin (Sasrin®resin), 3-(N-Fmoc-N-methoxy)propyl-amidomethyl resin (Weinreb amide resin).

In one specific aspect of the invention, the protected linear peptidomimetic compound of formula (II) has a structure of formula (IIa):

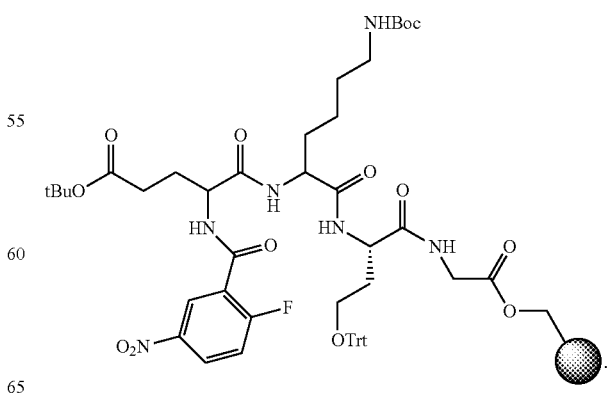

(IIa)

Protected Linear Peptidomimetic Compound of Formula (III)

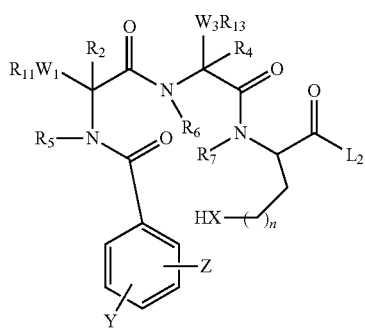

(III)

wherein $R_2$ and $R_4$ are independently hydrogen or $C_1$ to $C_6$ alkyl, or $W_1$ and $R_2$ together with the carbon atom to which they are attached form a cyclopropyl, cyclobutyl, cyclopentyl or cyclohexyl group, or $W_3$ and $R_4$ together with the carbon atom to which they are attached form a cyclopropyl, cyclobutyl, cyclopentyl or cyclohexyl group;

$R_5$, $R_6$ and $R_7$ are independently hydrogen or $C_1$ to $C_6$ alkyl;

Y is selected from the group consisting of hydrogen, $-NO_2$, $-COOR_8$, $-OC(R_8)_3$, $-SO_3R_8$, and $-SO_2NR_8$;

each $R_8$ is independently alkyl or aryl;

X is selected from the group consisting of O, N, S, P, Se, C, $C_1$ to $C_6$ alkylene, SO, $SO_2$ and NH;

Z is selected from the group consisting of F, Cl, Br and I;

$R_{11}$ and $R_{13}$ are independently hydrogen or a protecting group;

$W_1$ and $W_3$ are independently an amino acid side chain substituent of a natural or unnatural amino acid, less a hydrogen atom at the point of attachment to $R_{11}$ and $R_{13}$ respectively;

n is 0, 1, 2, 3, 4 or 5; and $L_2$ is selected from the group consisting of H, $NH_2$, OH, SH, COOH, $NH-CH_2-COOH$, $C_1$ to $C_6$ alkyl, and $C_1$ to $C_6$ aryl.

In one specific aspect of the invention, the protected linear peptidomimetic compound of formula (III) has a structure of formula (IIIa):

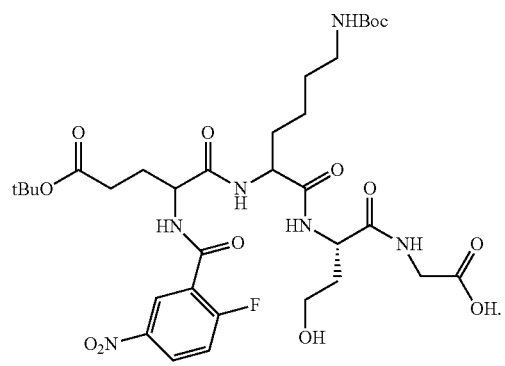

(IIIa)

Protected β-Turn Peptidomimetic Cyclic Compound of Formula (IV)

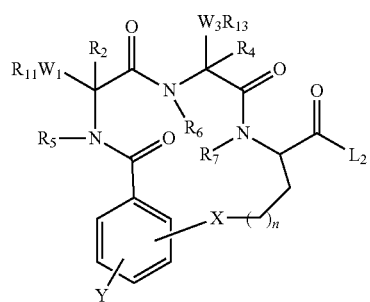

(IV)

wherein $R_2$ and $R_4$ are independently hydrogen or $C_1$ to $C_6$ alkyl, or $W_1$ and $R_2$ together with the carbon atom to which they are attached form a cyclopropyl, cyclobutyl, cyclopentyl or cyclohexyl group, or $W_3$ and $R_4$ together with the carbon atom to which they are attached form a cyclopropyl, cyclobutyl, cyclopentyl or cyclohexyl group;

$R_5$, $R_6$ and $R_7$ are independently hydrogen or $C_1$ to $C_6$ alkyl;

Y is selected from the group consisting of hydrogen, $-NO_2$, $-COOR_8$, $-OC(R_8)_3$, $-SO_3R_8$, and $-SO_2NR_8$;

each $R_8$ is independently alkyl or aryl;

X is selected from the group consisting of O, N, S, P, Se, C, $C_1$ to $C_6$ alkylene, SO, $SO_2$ and NH;

$R_{11}$ and $R_{13}$ are independently hydrogen or a protecting group;

$W_1$ and $W_3$ are independently an amino acid side chain substituent of a natural or unnatural amino acid, less a hydrogen atom at the point of attachment to $R_{11}$ and $R_{13}$ respectively;

n is 0, 1, 2, 3, 4 or 5; and $L_2$ is selected from the group consisting of H, $NH_2$, OH, SH, COOH, $NH-CH_2-COOH$, $C_1$ to $C_6$ alkyl, and $C_1$ to $C_6$ aryl.

In one specific aspect of the invention, the protected β-turn peptidomimetic cyclic compound of formula (IV) has a structure of formula (IVa):

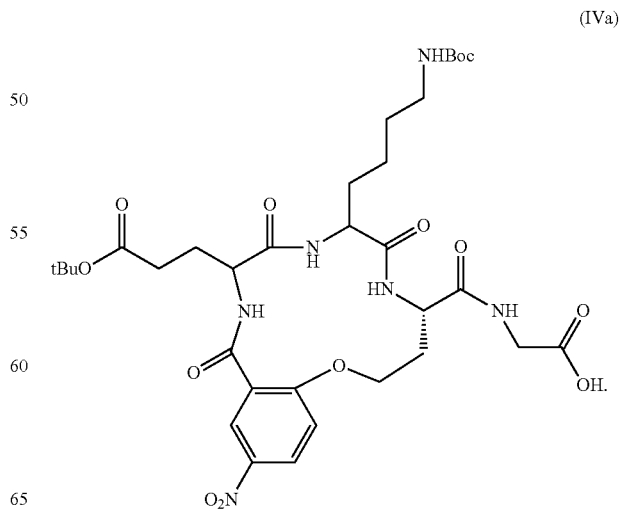

(IVa)

In certain embodiments, the present invention provides a method of preparing a β-turn peptidomimetic cyclic compound of structure D3. FIG. 2 shows exemplary reaction Scheme 2 which depicts a route to prepare β-turn peptidomimetic cyclic compound of structure D3 using a 2-chlorotrityl chloride (2-CTC) resin.

EXAMPLES

The following examples are merely illustrative of the present invention and should not be considered limiting the scope of the invention in any way, as these examples and other equivalents thereof will become apparent to those skilled in the art in light of the present disclosure and the accompanying claims. All percentages used in the application are percent weight by weight (w/w) unless otherwise noted.

Example 1

FIG. 2 (Scheme 2) illustrates the synthesis of Compound D3, which is one embodiment of β-turn peptidomimetic cyclic compound of formula (I). The synthesis was carried out using 2-Cl-Trt-Cl (2-CTC) resin as solid support.

Synthesis of Compound 2b can be carried out by standard stepwise Fmoc SPPS (solid phase peptide synthesis) procedures known in the art. Merrifield, (J. Am. Chem. Soc. 1964, 85, 2149); Vale et al., (Science, 1981, 213,1394-1397), in U.S. Pat. Nos. 4,305,872 and 4,316,891, Bodanszky et al. (Principles of Peptide Synthesis, $2^{nd}$ ed., Springer Verlag Berlin Heidelberg 1989) and Pieta and Marshall, (Chem. Comm. 1970, 650); (Houver-Weyl, Methods of Organic Chemistry. Vol E22a. Synthesis of Peptides and Peptidomimetics, Murray Goodman, Editor-in-Chief, Thieme. Stuttgart. New York 2002).

Loading of the 2-CTC resin 2 commonly takes place by nucleophilic substitution of the diphenyl-2'-chlorophenyl-chloromethane derivative.

1 g of 2-CTC resin (1.2 mmol/g) was swollen in 30 mL of dry dichloromethane (DCM) for 30 min. The solvent was filtered and a solution of Fmoc-Gly-OH (2 eq) and N,N-diisopropylethyl amine (DIPEA) (4 eq) in dry DCM (10 mL) was added to the resin. A small amount of N,N'-dimethylformamide (DMF) was also added to facilitate dissolution of the acid. The solution was stirred for 30 min at room temperature under nitrogen atmosphere. At the end of the reaction time, the resin was filtered and washed with a solution of DCM/DIPEA (3×5 min), DCM (3×5 min) and DMF (3×5 min). The loading of the amino acid was determined on a small amount of resin accurately dried and weighted by deprotecting of the N-terminal Fmoc group with 1,8-Diazabicycloundec-7-ene (DBU), and measuring the solution concentration of the liberated dibenzofluvene by UV spectroscopy as described by Gude et al (Lett. Pept. Sci. 2003, 9, 203).

After washing of the resin, the Fmoc protecting group was removed by treatment with 10 mL of 20% (v/v) piperidine in DMF for 30 min. The resin was filtered and washed with DMF (3×5 min) and DCM (3×5 min) to remove the excess of base. The deprotection reaction was monitored on a small amount of resin by a positive nynhydrin test (E. Kaiser et al, *Analytical Biochemistry* 1970, 34, 595)

The coupling of the subsequent amino acids, Fmoc-hSer (Trt)-OH, Fmoc-Lys(Boc)-OH and Fmoc-Glu(OtBu)—OH was performed in a stepwise manner alternating coupling reaction to a Fmoc deprotection cycle. In particular for coupling a solution of Fmoc protected amino acid (2 eq), HOBt (2 eq), DIC (2 eq) and DIPEA (4 eq) in DMF was added to resin and mixed for 1 h at room temperature. After each coupling cycle the resin was washed with DMF (3×5 min) and DCM (3×5 min) to remove the excess of reagents. The progress of each coupling was monitored by a negative ninhydrin test. Coupling of 2-fluoro-5-nitrobenzoic acid (2 eq) was performed using 2 equivalents of HBTU and DIEA (4 eq) in DMF. The resin was finally washed with DMF (3×5 min) and DCM (3×5 min), filtered and dried with a stream of nitrogen affording Compound 2c.

The cleavage of Compound 2d from the resin was performed by treating Compound 2c with a solution of DCM:TFA:TIS in the ratio of 97:1:2 (v/v). The solution was allowed to remain in contact with the resin for 2 minutes before filtering. This step was repeated five times. The filtrate was collected and the solvent removed under reduced pressure. The residual TIS was decanted and the product residue 2d was dried under nitrogen.

Product residue 2d was dissolved in a 9:1 solution of DCM:DMF at a concentration of 20 mg/mL, $K_2CO_3$ (2 eq) was subsequently added and the mixture stirred at 50° C. for 3 hours. The reaction was monitored by analytical RP-HPLC to ensure complete formation of the cyclic product. The following analytical, reverse-phase HPLC method was used for in-process control:

| | |
|---|---|
| Column | YMC $C_{18}$, 5 μm, 0.46 × 25 cm, or equivalent |
| Solvent A | 0.1% TFA in water |
| Solvent B | 0.1% TFA in acetonitrile |
| Flow Rate | 1.0 mL/min |
| Detection | 210 nm |
| Column Temperature | Ambient |
| Gradient | 5-35% B, duration 30 minutes |

The reaction mixture was then filtered over a Celite pad to eliminate the base, and the filter washed with THF. The filtrate was collected and evaporated under pressure at 60° C. to eliminate the DMF affording product 2e.

The product 2e was dissolved in a solution of 95% TFA in $H_2O$ for 1 hour. Complete deprotection of amino acids side chains was achieved. The solvent was concentrated under reduced pressure and the product precipitated with cold methyltertbutyl ether. Crude product D3 was purified by RP-HPLC on a C18 column using a gradient of acetonitrile in water, fractions containing the desired product were collected and lyophilized to afford Compound D3 as TFA salt at an overall yield of 40%.

The purified TFA salt of Compound D3 was exchanged to the HCl salt of Compound D3 by ion-exchange chromatography on Dowex resin. A solution in aqueous acetonitrile of the lyophilized pooled sub-lots obtained during the chromatographic purification was passed through a column packed with an excess of Dowex 1×2-100 (chloride form), which was subsequently washed with additional aqueous acetonitrile to recover the product.

The eluted peptide was collected, shell frozen and lyophilized to afford an off-white amorphous solid in 95% yield.

While the invention has been described and pointed out in detail with reference to operative embodiments thereof, it will be understood by those skilled in the art that various changes, modifications, substitutions, and omissions can be made without departing from the spirit of the invention. It is intended therefore, that the invention embrace those equivalents within the scope of the claims that follow.

What is claimed is:

1. A method of preparing a β-turn peptidomimetic cyclic compound of formula (I)

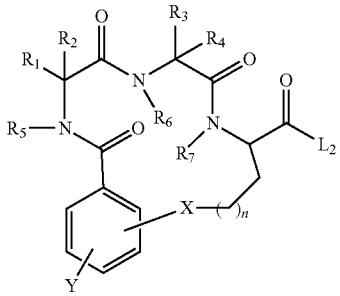

the method comprising steps of:
(a) providing a protected linear peptidomimetic compound of formula (III)

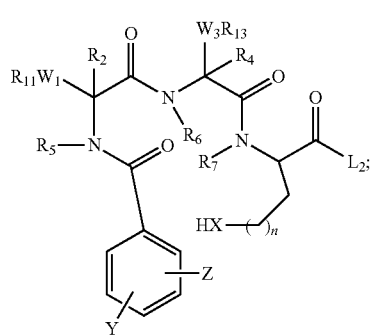

(b) cyclizing the protected linear peptidomimetic compound of formula (III) to form a protected β-turn peptidomimetic cyclic compound of formula (IV) by an intramolecular aromatic nucleophilic substitution

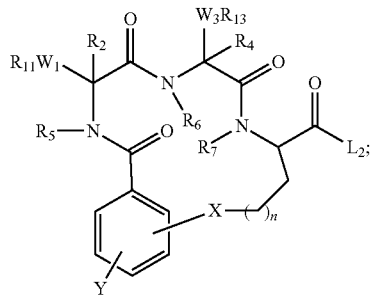

and
(c) deprotecting an amino acid side chain protecting group in the protected β-turn peptidomimetic cyclic compound of formula (IV);
wherein:
$R_1$ and $R_3$ are independently hydrogen, $C_1$ to $C_6$ alkyl, aryl, or an amino acid side chain substituent of a natural or unnatural amino acid;
$R_2$ and $R_4$ are independently hydrogen or $C_1$ to $C_6$ alkyl, or $R_1$ and $R_2$ together with the carbon atom to which they are attached form a cyclopropyl, cyclobutyl, cyclopentyl or cyclohexyl group, or $R_3$ and $R_4$ together with the carbon atom to which they are attached form a cyclopropyl, cyclobutyl, cyclopentyl or cyclohexyl group;
$R_5$, $R_6$ and $R_7$ are independently hydrogen or $C_1$ to $C_6$ alkyl;
Y is selected from the group consisting of hydrogen, $-NO_2$, $-COOR_8$, $-OC(R_8)_3$, $-SO_3R_8$, and $-SO_2R_8$;
each $R_8$ is alkyl or aryl;
X is selected from the group consisting of O, N, S, P, Se, C, C1 to C6 alkylene, SO, $SO_2$ and NH;
Z is selected from the group consisting of F, Cl, Br and I;
$R_{11}$ and $R_{13}$ are independently hydrogen or a protecting group;
$W_1$ and $W_3$ are independently an amino acid side chain substituent of a natural or unnatural amino acid, less a hydrogen atom at the point of attachment to $R_{11}$ and $R_{13}$ respectively;
n is 0, 1, 2, 3, 4 or 5; and
$L_2$ is H, OH, SH, COOH, $NH-CH_2-COOH$, $C_1$ to $C_6$ alkyl, or $C_1$ to $C_6$ aryl.

2. The method of claim 1 wherein the β-turn peptidomimetic cyclic compound of formula (I) has a macrocyclic ring of from 14 to 16 ring atoms.

3. The method of claim 1 wherein $R_1$ and $R_3$ are independently a side chain substituent of two different amino acids.

4. The method of claim 3 wherein $R_1$ and $R_3$ are independently a side chain substituent of lysine, glutamic acid, tyrosine, isoleucine, asparagine, arginine or threonine.

5. The method of claim 1 wherein $R_1$ and $R_3$ are independently a side chain substitutent of glutamic acid or lysine.

6. The method of claim 1 wherein $R_1$ and $R_3$ are independently a side chain substitutent of isoleucine or arginine 7. The method of claim 1 wherein $R_{11}$ and $R_{13}$ are independently selected from the group consisting of trifluoroacetyl, formyl, acetyl, t-butyloxycarbonyl (BOC), cyclohexyloxycarbonyl, fluorenyl-9-methoxy-carbonyl (Fmoc), benzyloxycarbonyl (Cbz), Cbz derivatives, triphenyl, methyl, benzyl, allyloxycarbonyl, tert-butyl, alkyl sliane and allyl.

8. The method of claim 1 wherein $R_1$ is a side chain substitutent of glutamic acid and $R_{11}$ is allyl or tert-butyl.

9. The method of claim 8 wherein $R_{11}$ is tert-butyl.

10. The method of claim 1 wherein $R_3$ is a side chain substitutent of lysine and $R_{13}$ is benzyloxycarbonyl, allyloxycarbonyl, or tert-butyloxycarbonyl (BOC).

11. The method of claim 10 wherein $R_{13}$ is tert-butyloxycarbonyl (BOC).

12. The method of claim 1 wherein $R_2$ and $R_4$ are independently hydrogen or $C_1$ to $C_6$ alkyl.

13. The method of claim 1 wherein $R_5$, $R_6$ and $R_7$ are hydrogen.

14. The method of claim 1 wherein X is O, S or NH.

15. The method of claim 1 wherein L is $NH-CH_2-COOH$.

16. The method of claim 1 wherein n is 1.

17. The method of claim 1 wherein Y is attached to the benzene ring of the formulas at the meta position relative to the point of attachment of the amide group.

18. The method of claim 1 wherein Y is $-NO_2$.

19. The method of claim 1 wherein Z is attached to the benzene ring of the formulas at the ortho position relative to the point of attachment of the amide group.

20. The method of claim 1 wherein Z is F.

21. The method of claim 1 wherein the protected linear peptidomimetic compound of formula (III) is obtained from cleaving a protected linear peptidomimetic compound of formula (II) from a solid support in the presence of an acid, a base or a nucleophile, wherein the protected linear peptidomimetic compound of formula (II) has the following structure:

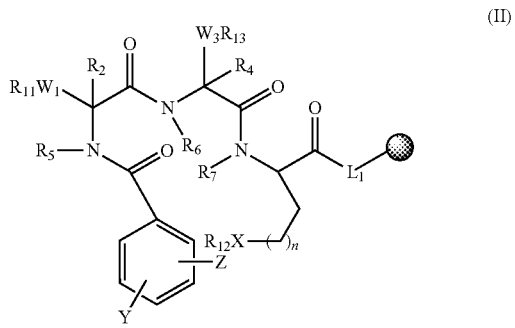

(II)

wherein $L_1$ is null, NH, O, S, COO—, NH—$CH_2$—COO—, $C_1$ to $C_6$ alkylene, or $C_1$ to $C_6$ arylene; and $R_{12}$ is hydrogen or a protecting group.

22. The method of claim 21 wherein $R_{12}$ is a protecting group.

23. The method of claim 21 wherein X is O and $R_{12}$ is trityl or tert-butyldimethylsilane (TBDMS).

24. The method of claim 21 wherein X is S and $R_{12}$ is trityl.

25. The method of claim 21 wherein X is NH and $R_{12}$ is 4-methyltrityl (Mtt).

26. The method of claim 21 wherein the cleaving of the protected linear peptidomimetic compound of formula (II) does not cause deprotection of any protected functional group $R_{11}$ and $R_{13}$ present in formula (II).

27. The method of claim 21 wherein the cleaving of the protected linear peptidomimetic compound of formula (II) is performed under mild acidic condition.

28. The method of claim 27 wherein the mild acidic condition comprises from about 0.01% to about 50% (v/v) of trifluoro acetic acid (TFA).

29. The method of claim 21 wherein the cleaving of the protected linear peptidomimetic compound of formula (II) is carried in a polar aprotic solvent.

30. The method of claim 29 wherein the polar aprotic solvent comprises dichloromethane, acetonitrile or tetrahydrofurane and mixture thereof.

31. The method of claim 21 wherein the cleaving of the protected linear peptidomimetic compound of formula (II) further comprises a scavenger.

32. The method of claim 31 wherein the scavenger comprises triisoprpylsilane (TIS), thioanisol, trialkylsilane, or mixtures thereof.

33. The method of claim 31 wherein the scavenger is triisopropylsilane (TIS).

34. The method of claim 31 wherein the cleaving of the protected linear peptidomimetic compound of formula (II) is performed in a solution comprising less than 10% of a mixture of TFA and TIS in a ratio by volume of from 1:1 to 1:5.

35. The method of claim 21 wherein the solid support is a resin comprising a functional group selected from the group consisting of 2-chlorotrityl chloride (2-CTC), 4-hydroxymethyl-3-methoxyphenoxybutirric acid MBHA (HMPB-MBHA), 9 Fmoc-amino-xanthen-3-yloxy-Merrifield resin (Sieber Amide), trityl alcohol, 4-methyltrityl chloride, 4-methoxytrityl chloride, 4-(2',4'-Dimethoxyphenyl-hydroxymethyl)-phenoxy resin (Rink acid resin), 2-methoxy-4-alkoxybenzyl alcohol resin, 3 (N-Fmoc-N-methoxy)propylamidomethyl resin (Weinreb amide resin).

36. The method of claim 35 wherein the resin has a functional group loading of at least 0.75 mmol/g.

37. The method of claim 35 wherein the resin has a functional group loading of from 1.0 to 2.0 mmol/g.

38. The method of claim 35 wherein the resin is an insoluble polymer.

39. The method of claim 35 wherein the resin is a crosslinked polystyrene divinylbenzene co-polymer.

40. The method of claim 1 wherein the cyclizing is performed in solution phase.

41. The method of claim 1 wherein the cyclizing is performed in the presence of a base.

42. The method of claim 41 wherein the base comprises $K_2CO_3$, $CsCO_3$, CsF, tetrabutylammonium fluoride (TBAF), tetramethylguanidine (TMG), or mixtures thereof.

43. The method of claim 1 wherein the cyclizing is performed in a polar protic solvent.

44. The method of claim 43 wherein the polar protic solvent comprises acetonitrile, tetrahydrofurane, DMF, mixture of DCM/DMF, or mixtures thereof.

45. The method of claim 44 wherein the mixture of DCM/DMF is used in the ratio of from 5:95 to 95:5.

46. The method of claim 1 wherein the cyclizing is performed in the absence of water and methanol.

47. The method of claim 1 wherein the cyclizing is performed at a concentration lower than 0.05M of the protected linear peptidomimetic compound of formula (III).

48. The method of claim 1 wherein the cyclizing is performed at a temperature from 25° C. to 60° C.

49. The method of claim 1 wherein the deprotecting is performed under a strong acidic condition.

50. The method of claim 1 wherein the strong acidic condition comprises greater than 50% TFA.

51. The method of claim 1 wherein the deprotecting further comprises a scavenger.

52. A method of preparing a β-turn peptidomimetic cyclic compound of formula D3

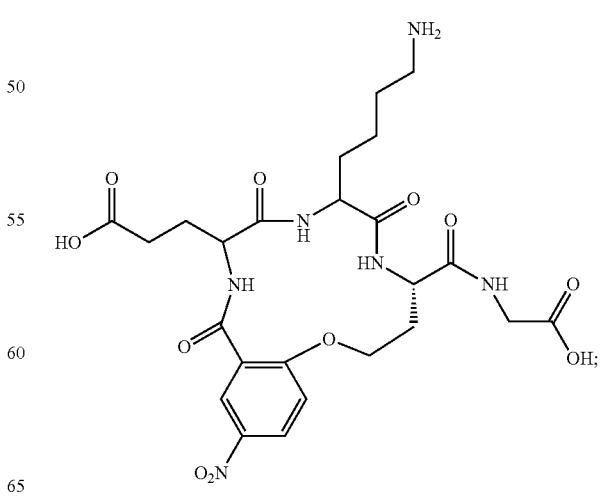

D3 the method comprising steps of:
(a) providing a protected linear peptidomimetic compound of formula (IIIa)

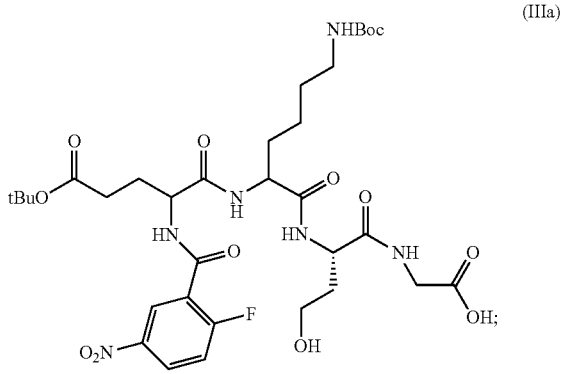 [SMILES: CC(C)(C)OC(=O)CCC(NC(=O)c1cc([N+](=O)[O-])ccc1F)C(=O)NC(CCCCNC(=O)OC(C)(C)C)C(=O)N[C@@H](CCO)C(=O)NCC(=O)O]

(IIIa)

(b) cyclizing the protected linear peptidomimetic compound of formula (IIIa) to form a protected β-turn peptidomimetic cyclic compound of formula (IVa) by an intramolecular aromatic nucleophilic substitution

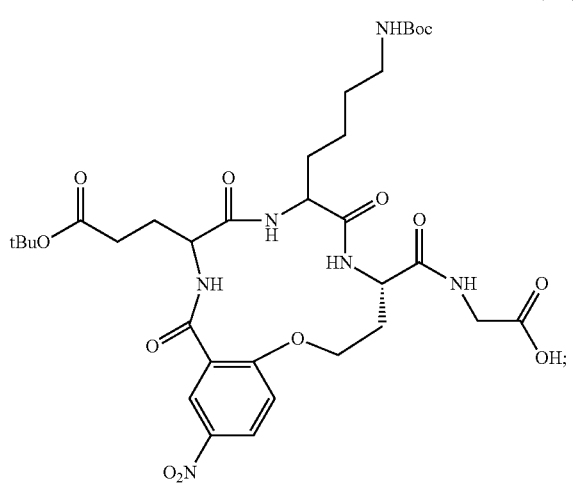

(IVa)

and (c) deprotecting an amino acid side chain protecting group in the protected β-turn peptidomimetic cyclic compound of formula D3.

53. The method of claim 52 wherein the protected linear peptidomimetic compound of formula (IIIa) is obtained from cleaving a protected linear peptidomimetic compound of formula (IIa) from a solid support in the presence of an acid, a base or a nucleophile, wherein the protected linear peptidomimetic compound of formula (IIa) has the following structure:

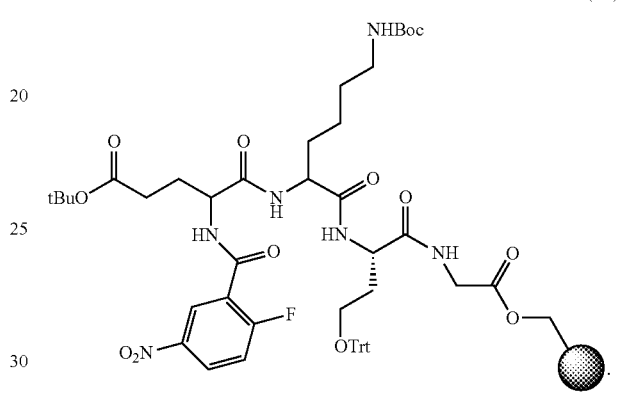

(IIa)

54. The method of claim 53 wherein the solid support is a resin comprising a functional group selected from the group consisting of 2-chlorotrityl chloride (2-CTC), 4-hydroxymethyl-3-methoxyphenoxybutirric acid MBHA (HMPB-MBHA), 9-Fmoc-amino-xanthen-3-yloxy-Merrifield resin (Sieber Amide), trityl alcohol, 4-methyltrityl chloride, 4-methoxytrityl chloride, 4-(2',4'-Dimethoxyphenyl-hydroxymethyl)-phenoxy resin (Rink acid resin), 2-methoxy-4-alkoxybenzyl alcohol resin, 3-(N-Fmoc-N-methoxy)propyl-amidomethyl resin (Weinreb amide resin)

* * * * *